United States Patent [19]

Good et al.

[11] Patent Number: 5,595,653
[45] Date of Patent: Jan. 21, 1997

[54] MICROCOLUMN FOR EXTRACTION OF ANALYTES FROM LIQUIDS

[75] Inventors: Thomas J. Good, Sierra Madre; Alan F. Redmond, Temple City, both of Calif.

[73] Assignee: Cera, Inc., Baldwin Park, Calif.

[21] Appl. No.: 275,781

[22] Filed: Jul. 15, 1994

[51] Int. Cl.$^6$ .......................... B01D 24/00; B01D 24/20; B01D 39/06; B01D 15/00
[52] U.S. Cl. .................. 210/289; 210/198.2; 210/263; 210/287; 210/291; 210/435; 210/446; 210/456; 210/483; 210/484; 210/488; 210/502.1; 210/503; 422/58; 422/59; 422/60; 422/69; 422/70; 422/101; 422/102
[58] Field of Search ........................ 210/435, 446, 210/456, 483, 484, 488, 489, 490, 491, 502.1, 503, 505, 198.2, 263, 283, 287, 289, 290, 291; 422/58, 59, 60, 69, 70, 101, 102, 104; 435/311; 436/527, 177, 178; 530/412, 413, 416, 417; 502/401, 405

[56] References Cited

U.S. PATENT DOCUMENTS

| | | |
|---|---|---|
| 2,744,067 | 5/1956 | Higuchi . |
| 3,625,652 | 12/1971 | Fujimoto et al. . |
| 4,270,921 | 6/1981 | Graas . |
| 4,341,635 | 7/1982 | Golias ........................... 210/656 |
| 4,476,713 | 10/1984 | Aldredson ...................... 210/656 |
| 4,650,784 | 3/1987 | Ramsden et al. ............... 502/407 |
| 4,774,058 | 9/1988 | Mehl ............................... 422/101 |
| 4,820,276 | 4/1989 | Moreno .......................... 604/190 |
| 4,874,518 | 10/1989 | Kirkland et al. ............... 210/198.2 |
| 4,906,378 | 3/1990 | Hagen et al. ................... 210/635 |
| 5,032,261 | 7/1991 | Pyper ............................. 210/137 |
| 5,039,419 | 8/1991 | Bradshaw et al. .............. 210/502.1 |
| 5,049,284 | 7/1991 | Motoki et al. .................. 210/682 |
| 5,137,626 | 8/1992 | Parry et al. .................... 210/198.2 |
| 5,238,621 | 8/1993 | Hagen et al. ................... 210/198.2 |
| 5,266,193 | 11/1993 | Kimura et al. ................. 210/198.2 |
| 5,279,742 | 1/1994 | Markell et al. ................. 210/638 |
| 5,318,703 | 6/1994 | Heiligman ...................... 210/264 |
| 5,366,632 | 11/1994 | Balsimo et al. ................ 210/777 |
| 5,368,729 | 11/1994 | Stefkovich et al. ............ 210/282 |
| 5,391,298 | 2/1995 | Pieper et al. ................... 210/638 |
| 5,403,489 | 4/1995 | Hagen et al. ................... 210/502.1 |
| 5,415,779 | 5/1995 | Markell et al. ................. 210/198.2 |
| 5,427,683 | 6/1995 | Gershon et al. ................ 210/264 |
| 5,433,847 | 7/1995 | Rice ................................ 210/198.2 |
| 5,454,951 | 10/1995 | Hoopman ....................... 210/456 |
| 5,529,686 | 6/1996 | Hagen et al. ................... 210/505 |
| 5,538,634 | 7/1996 | Pfiffner et al. ................. 210/502.1 |

OTHER PUBLICATIONS

Whatman, "Media for Clinical Diagnostics," Second Issue (Undated).
"Empore Extraction Disk Cartridges," 3M, 1993.
"SPEC," Toxi–Lab, Inc., 1992.
"Extraction Station," J. T. Baker, *LC–GC,* vol. 12, No. 3 (Mar. 1994), p. 258.

*Primary Examiner*—John Kim
*Attorney, Agent, or Firm*—Jeffrey G. Sheldon; Sheldon & Mak, Inc.

[57] ABSTRACT

An apparatus for extracting an analyte from a liquid sample, comprises a microcolumn having a microparticulate media therein, the media being sandwiched between two compression layers. Preferably, the compression layers comprise a binder-free glass fiber, held in the microcolumn by upper and lower polypropylene mesh.

19 Claims, 1 Drawing Sheet

MICROCOLUMN FOR EXTRACTION OF ANALYTES FROM LIQUIDS

BACKGROUND

The present invention relates to microcolumns for extraction of an analyte from a liquid sample, and particularly extraction of an analyte from biological fluids.

Accurate and inexpensive detection of analytes present in liquid samples, for example in biological fluids, such as blood and urine, is important to health care. Tests for analytes in blood and urine are conducted to monitor the health of patients, detect the presence of disease conditions, and monitor for the use of illegal or restricted drugs. For example, doctors, when administering drugs such as antiarrythymics, asthmatic drugs, insulin, and anticoagulants, check the drug content of the blood to regulate the dosages of the patient. Drugs that can be abused, such as heroin, marijuana, cocaine, and codeine, can be tested to determine abuse of the drug, such as by employees and by athletes.

A technique used for detection of analytes includes selectively extracting the analyte from the biological fluid onto a solid media. The analyte is then removed from the solid media by a suitable elution liquid, and tests are conducted to determine whether the analyte is present in the eluent liquid, such as by gas or liquid chromatography.

Prior art extraction columns have been effectively used. For example, it is known to use particulate silica as the solid media in a column. In addition, silica has been provided embedded within an inert matrix of polytetrafluoroethylene ("PTFE") in the form of an extraction disk, which can be preloaded in a plastic barrel.

A problem with use of PTPE to hold the silica is that PTFE is hydrophobic and can require preconditioning with alcohol and high pressure so that the aqueous sample can flow therethrough. This increases the time and manpower required for the analysis.

Although these prior art devices can be effective, it is desirable to improve on these devices. It is desirable that the extraction device be fast, remove a high percentage of the analyte from the sample, be transportable, storable without damage, and be inexpensive. Moreover, it is desirable that any such device be compatible with existing automated equipment, and not leach into the biological fluid or the eluent liquid, any compound that could interfere with the analytical results.

Moreover, it is desirable to minimize the volume of biological fluid and wash eluent liquid. By minimizing the liquid volume, a more concentrated sample is obtained for analysis, the sensitivity of the test is enhanced, and less biological fluid needs to be obtained from the subject. High yields from the biological fluid with minimum elution volumes can be obtained by maintaining uniform flow through the extraction media, with no channeling and no dead volume.

SUMMARY

The present invention is directed to an extraction apparatus that meets these needs. The apparatus is useful for extracting an analyte from a liquid sample and comprises a container, typically a microcolumn, having an entrance, an opposed exit, and a passage therebetween for passage of a liquid sample containing an analyte therethrough. Within the passage is a thin layer of a microparticulate extraction media, typically silica particles. The media is selected for extracting the analyte from the liquid sample. The extraction media has a small particle size of less than 20 microns, which is provided in a very thin layer, so that the ratio of the effective diameter of the extraction media layer to the thickness of the layer is at least 10.

The extraction media is sandwiched between upper and lower compression layers, which compress the silica extraction media therebetween. The compression layers are sufficiently porous that the liquid sample can flow therethrough, and are formed from a flexible, hydrophilic material. This is in contrast to the prior art preformed disks, which are made of polytetrafluoroethylene, which is hydrophobic, and thus slows down the flow of sample through the extraction media and utilizes preconditioning. The compression layer has a pore size less than the particle size of the extraction media, and is preferably formed of a spongy, glass fiber, having no binder.

Preferably the microcolumn also includes an upper mesh flow distributor above the upper compression layer, and a lower mesh flow distributor below the lower compression layer, sandwiching the compression layers and the layer of extraction media therebetween. The flow distributors hold the extraction media and the compression layers in the microcolumn and help distribute flow of the liquid sample to avoid channeling.

Due to the combination of the very thin layer of extraction media and the compression layers, rapid extraction of an analyte from a biological fluid can be obtained, with very small volumes of biological fluid, i.e., less than 0.5 ml, and only very small samples of elution liquid are needed, on the order of 0.5 to 0.75 ml. In addition, the extraction device of the present invention is inexpensive to use and manufacture, is stable during storage and transportation, and is compatible with existing automated equipment.

DRAWINGS

These and other features, aspects, and advantages of the present invention can be better understood with reference to the following description, appended claims, and accompanying drawings, where:

DESCRIPTION

Figure 1:
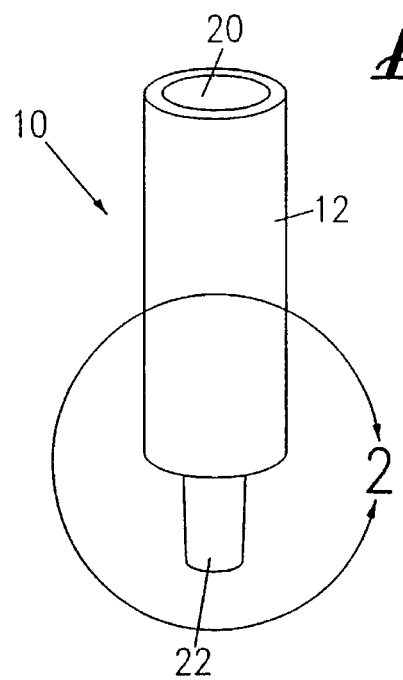
FIG. 1 is a perspective view of one version of a microcolumn according to the present invention.
Figure 2:
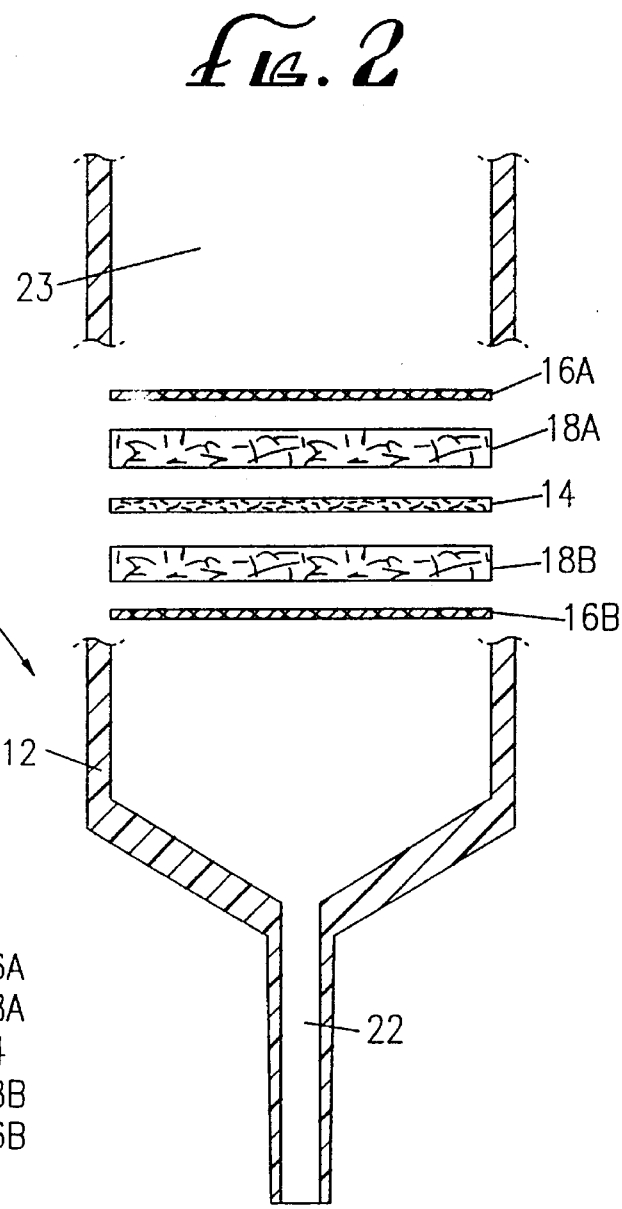
FIG. 2 is a side elevation view, exploded, partly in section, of region 2 of the microcolumn of FIG. 1.
Figure 3:
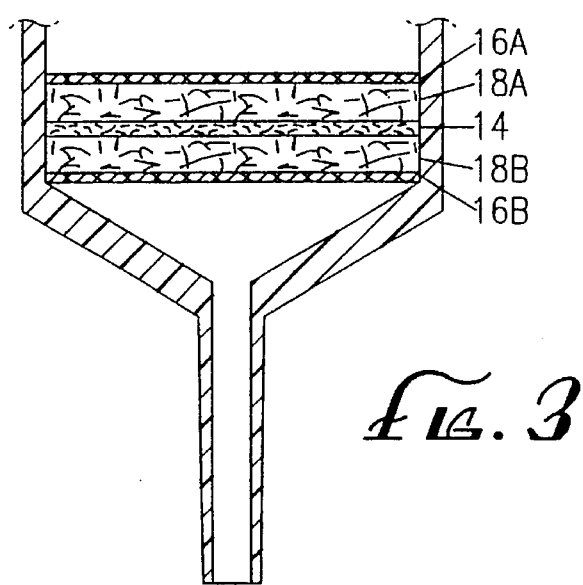
FIG. 3 is a side elevation view, partly in section, of the microcolumn of FIG. 1 in region 2 of FIG. 1.

An apparatus 10 for extracting an analyte from a liquid sample is shown in FIGS. 1–3. The apparatus 10 comprises a microcolumn 12, which serves as a container for an extraction sandwich system. The extraction system is comprised of a five-layer sandwich construction, that includes (i) a thin extraction layer 14 of microparticulate solid extraction medium, (ii) an upper flow distributor 16a, (iii) a lower flow distributor 16b, and two compression layers, (iv) an upper compression layer 18a between the upper flow distributor 16a and the extraction layer 14, and (v) a lower compression layer 18b between the lower flow distributor 16b and the extraction layer 14.

The microcolumn 12 has generally a tubular configuration, and has an entrance 20, an opposed exit 22, and a passage 23 therebetween. The passage 23, which is also referred to as a central bore, contains the extraction system.

The exit 22 is preferably in the form of a luer-lock, which allows the apparatus 10 to be used with conventional automated extraction apparatus, such as a vacuum extraction apparatus, which are designed to receive an extraction column having a luer-lock.

A liquid sample flows in the direction of arrow 26 shown in FIG. 2 through the passage 23.

The portion of the microcolumn 12 above the extraction sandwich system serves as a reservoir for the liquid sample, from which an analyte is to be extracted, and also a reservoir for an eluent liquid.

All of the components of the apparatus 10 are made of materials that are substantially inert to biological fluids so that when blood or urine is passed through the apparatus 10, substantially nothing passes from the apparatus 10 into the blood or urine. Preferably, the microcolumn 12 is made of polypropylene, or alternatively, a fluorinated polymer.

A typical microcolumn according to the present invention has an internal diameter of about ¼ to 1 inch, and a length, excluding the luer tip, of about 2 to about 6 inches.

The microcolumn 12 need not have the shape shown in the figures. For example, it need not be cylindrical in horizontal cross-section. In addition, in one embodiment of the invention, the entrance 20 can be designed to receive a luer-lock extension so that a reservoir containing a liquid sample can be piggybacked on top of the microcolumn 12.

The extraction media 14 is formed of silica, such as a silica gel, constituted pure glass, modified silica, or polymeric resin such as divinyl benzene. The media particles are of small particle size, preferably having a number average of particle size of less than 20 microns, and more preferably, less than 10 microns. A suitable silica extraction media is described in U.S. Pat. No. 4,650,714, which is incorporated herein by reference. A preferred microparticulate silica extraction media is available from J.T. Baker Chemical Company of Phillipsburg, N.J., and is sold under their catalog number 7049-01.

Because of the small particle size of the silica, and because it is not impregnated into a hydrophobic layer such as polytetrafluoroethylene, it is possible to have a very thin extraction layer. Typically, the thickness of the extraction layer is less than 1 mm, and typically from about 0.1 to about 0.8 mm. Preferably, the ratio of the effective diameter of the extraction layer to the thickness of the extraction layer is at least 10, and more preferably at least 15. By "effective diameter" there is meant:

$$D_{eq}=(4A/\pi)^{1/2}$$

where $D_{eq}$ is the equivalent diameter and A is the cross-sectional surface area of the bore of the microcolumn 12.

Preferably, the silica extraction media is placed in the microcolumn 12 using a slurry packing technique, utilizing as the carrier isopropanol.

The chief purpose of the compression layers 18 is to hold the extraction media in place and compressed as a thin extraction layer. Accordingly, the compression layers 18 have a pore size less than the particle size of the silica extraction media. They are sufficiently porous that the liquid sample can flow therethrough, and are composed of a flexible, hydrophilic material. Preferably the compression layers 18 are resilient or "spongy" to hold the microparticles in place. A preferred pore size for the compression layers is less than 5 microns, and more preferably less than 3 microns. The compression layers 18 generally are of the same thickness, having a thickness typically of from about ¼ to about 1 mm, and preferably about ½ mm.

A suitable compression layer comprises a glass microfiber media made of analytically clean material. Suitable materials, which are available from Whatman Specialty Products, Inc. of Fairfield, N.J., include a borosilicate glass fibers that are analytically clean and include no binder. This material, when purchased, has a smooth side and a rough side, where the smooth side is of lower porosity than the rough side. Preferably, it is the smooth side that is placed in contact with the microparticles of the extraction layer 14.

The flow distributors 16, which are formed of a flexible mesh material, help provide uniform flow of the sample through the column, and physically retain the compression layers and microparticulate material in place in the column. Preferably, the mesh is 200 mesh or smaller (i.e., has a mesh number of 200 or higher). It is made of polypropylene, or alternatively, polytetrafluoroethylene. A suitable material is available from Tetko, Inc. of Briarcliff Manor, N.Y., under catalog number 5-420134.

As shown in FIG. 3, the lower flow distributor 16b seats against the sloped bottom portion of the microcolumn. The upper flow distributor 16a is sized so that it is held in the bore of the microcolumn 12 by a compression fit.

As described, the apparatus 10 is easy and inexpensive to manufacture, is transportable, and efficiently and effectively removes analytes from liquid samples, requiring only small amounts of the liquid sample and small amounts of eluent fluid. The microcolumn can easily be injected molded. Further, the alcohol conditioning step required with the PTFE silica media is not required, thereby reducing the labor costs and time required for analyzing a sample.

Although the present invention has been described in considerable detail with reference to certain preferred versions thereof, other versions are possible. For example, the apparatus 10 is not limited to use with biological fluids, but can be used, for example, for testing ground water, drinking water, and other liquids for contaminants.

In addition, the extraction media does not have to be homogenous, but rather a different extraction media can be used in a single bed, or the apparatus can include multiple beds of extraction media for extracting different analytes from samples.

Therefore, the spirit and scope of the appended claims should not be limited to the description of the preferred versions contained herein.

What is claimed is:

1. Apparatus for extracting an analyte from a liquid sample comprising:
   a) a container having an entrance, an exit, and a passage therebetween for passage of a liquid sample containing an analyte therethrough;
   b) within the passage, a thin layer of microparticulate extraction media for extracting the analyte from the liquid sample, wherein:
      (i) the extraction media layer has a top surface, a bottom surface, and a peripheral edge,
      (ii) the extraction media has a particle size of less than 20 microns,
      (iii) the ratio of the effective diameter of the extraction media layer to the distance between its top and bottom surfaces is at least 10, and
      (iv) the extraction media layer is oriented in the passage so that liquid flows through the extraction media layer from its top surface to the bottom surface;
   c) an upper compression layer at the top surface of the extraction media layer and a lower compression layer at the bottom surface of the extraction media layer, the two compression layers pressing the extraction media therebetween, the compression layers being sufficiently porous that the liquid sample flows therethrough, the compression layers being formed of a flexible, hydrophilic, microfiber material and having a pore size less than the particle size of the extraction media;

d) an upper mesh flow distributor above the upper compression layer for distributing flow of the liquid sample uniformly to the extraction media layer top surface; and e) a lower mesh flow distributor below the lower compression layer.

2. The apparatus of claim 1 wherein the extraction media is slurry packed into the container.

3. The apparatus of claim 1 wherein the layer of extraction media is cylindrical.

4. The apparatus of claim 1 wherein the distance between the top and bottom surfaces of the layer of extraction media is less than 1 mm.

5. The apparatus of claim 4 wherein the distance between the top and bottom surfaces of the layer of extraction media is from 0.2 to 0.9 mm.

6. The apparatus of claim 1 wherein the compression layers are formed of the same material.

7. The apparatus of claim 1 wherein the upper mesh flow distributor holds the compression layers and the extraction media layer in the container.

8. The apparatus of claim 1, wherein the extraction media is silica.

9. The apparatus of claim 1 wherein the container includes an inner wall in contact with the peripheral edge of the media layer.

10. Apparatus for extracting an analyte from a liquid sample comprising:

a) a microcolumn having an entrance, an opposed exit, and a passage for passage of the liquid sample therethrough;

b) within the passage, a thin layer of microparticulate silica extraction media for the analyte, wherein:
 (i) the extraction media layer has a top surface, a bottom surface, and a peripheral edge,
 (ii) the extraction media has a particle size of less than 20 microns,
 (iii) the ratio of the effective diameter of the extraction media layer to the thickness of the extraction media layer is at least 10, and
 (iv) the extraction media layer is oriented in the passage so that liquid flows through the layer from its top surface to the bottom surface;

c) an upper compression layer at the top surface of the extraction media layer and a lower compression layer at the bottom surface of the extraction media layer, the compression layers pressing the silica extraction media therebetween, the compression layers being sufficiently porous that the liquid sample flows therethrough, the compression layers being formed of a flexible, hydrophilic, glass fiber and having a pore size less than the particle size of the silica extraction media;

d) an upper mesh flow distributor above the upper compression layer for distributing flow of the liquid sample uniformly to the extraction media layer top surface; and e) a lower mesh flow distributor below the lower compression layer.

11. The apparatus of claim 10 wherein the glass fiber is binder free.

12. The apparatus of claim 10 wherein the pore size of the compression layers is less than 5 microns.

13. The apparatus of claim 12 wherein the pore size of the compression layers is less than 3 microns.

14. The apparatus of claim 10 wherein the apparatus is made of materials substantially inert to biological fluids so that when blood or urine is passed through the apparatus, substantially nothing passes from the apparatus into the blood or urine.

15. Apparatus for extracting an analyte from a liquid sample comprising:

a) a polypropylene, microcolumn having an entrance, an opposed exit, an inner wall, and a central bore therethrough for passage of a liquid sample containing an analyte therethrough;

b) within the bore, a thin layer of microparticulate silica extraction media adapted for extracting the analyte from the liquid sample, the extraction media having a particle size of less than 20 microns, the extraction media having a top surface facing the entrance and a bottom surface facing the exit, the ratio of the diameter of the extraction media layer to the thickness of the layer being at least 10, the inner wall of the microcolumn being in contact with the peripheral edge of the extraction media layer;

c) an upper compression layer and a lower compression layer pressing the silica extraction media therebetween, the compression layers being sufficiently porous that the liquid sample flows therethrough and into the extraction media layer top surface and out of the extraction media layer bottom surface, the compression layers being formed of a flexible, hydrophilic, substantially binder free glass fiber and having a pore size less than the particle size of the silica extraction media; and d) an upper mesh flow distributor above the upper compression layer and a lower mesh flow distributor below the lower compression layer sandwiching the compression layers and the layer of extraction media therebetween, the flow distributors holding the extraction media and the compression layers in the microcolumn, the upper mesh flow distributor distributing liquid sample uniformly across the top surface of the extraction media layer.

16. The apparatus of claim 15 wherein the mesh size of the flow distributors is at least 200 mesh.

17. Apparatus for extracting an analyte from a liquid sample comprising:

a) a container having an entrance, an exit, and a passage therebetween for passage of a liquid sample containing an analyte therethrough;

b) within the passage, a thin layer of microparticulate extraction media for extracting the analyte from the liquid sample, wherein:
 (i) the extraction media layer has a top surface, a bottom surface, and a peripheral edge,
 (ii) the extraction media has a particle size of less than 20 microns,
 (iii) the distance between the top and bottom surfaces of the extraction media layer is less than 1 mm, and
 (iv) the extraction media layer is oriented in the passage so that liquid flows through the layer from its top surface to the bottom surface;

c) an upper compression layer at the top surface of the extraction media layer and a lower compression layer at the bottom surface of the extraction media layer, the two compression layers pressing the extraction media therebetween, the compression layers being sufficiently porous that the liquid sample can flow therethrough, the compression layers being formed of a flexible, hydrophilic, microfiber material and having a pore size less than the particle size of the extraction media;

d) an upper mesh flow distributor above the upper compression layer for distributing flow of the liquid sample uniformly to the extraction media layer top surface; and e) a lower mesh flow distributor below the lower compression layer.

18. The apparatus of claim 17 wherein the distance between the top and bottom surfaces of the extraction media layer is from 0.2 to 0.9 min.

19. The apparatus of claim 17 wherein the upper mesh flow distributor holds the compression layers and the extraction media layer in the container.

* * * * *